(12) United States Patent
Fu et al.

(10) Patent No.: US 12,138,679 B2
(45) Date of Patent: Nov. 12, 2024

(54) BENDING TOOLS AND METHODS OF USE THEREOF

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Rick Fu, Randolph, MA (US); Matthew D. Cunningham, Lakeville, MA (US); Allison Marie Stauffer, Brighton, MA (US); Geoffrey Ian Karasic, Milton, MA (US); Belin Mirabile, Memphis, TN (US); Han Teik Yeoh, Hopkinton, MA (US); Fabiano Paiva-Filho, Memphis, TN (US)

(73) Assignees: Smith & Nephew, Inc., Mempphis, TN (US); Smith & Nephew Orthopaedics AG, Baar (CH); Smith & Nephew Asia Pacific Pte. Limited, Singapore (SG)

( * ) Notice: Subject to any disclaimer, the term of this patent is extended or adjusted under 35 U.S.C. 154(b) by 369 days.

(21) Appl. No.: 17/552,547

(22) Filed: Dec. 16, 2021

(65) Prior Publication Data
US 2022/0161306 A1     May 26, 2022

Related U.S. Application Data

(63) Continuation-in-part of application No. PCT/US2020/035675, filed on Jun. 2, 2020.
(Continued)

(51) Int. Cl.
*B21D 9/12* (2006.01)

(52) U.S. Cl.
CPC .................................. *B21D 9/125* (2013.01)

(58) Field of Classification Search
CPC .......... B21D 9/125; B21D 7/06; B21D 7/063; B21F 1/00; B21F 1/06; H01R 4/16; H01R 43/28
See application file for complete search history.

(56) References Cited

U.S. PATENT DOCUMENTS 2,824,475 A * 2/1958 Rolando .................... B21F 1/06
                                                      72/457
3,147,651 A * 9/1964 Seigford ................ B21D 7/063
                                                      72/388
(Continued)

OTHER PUBLICATIONS

European Application No. 20746483.5-1113 Examination Report dated Jan. 2, 2022.
(Continued)

*Primary Examiner* — Teresa M Ekiert
(74) *Attorney, Agent, or Firm* — ArentFox Schiff LLP; Joseph M. Maraia; Marlo Schepper Grolnic

(57) ABSTRACT

A single-patient-use disposable tool comprises a molded, single-piece body with a curved upper surface having a predetermined bend radius for bending a needle slidably disposed in a sheath. A distal end of the curved surface has a slot for insertion of a tip of a needle, while the proximal end of the curved surface has a guide member for slidably receiving the sheath. Two finger loops or similar ergonomic features allow the user to rotate the bending tool relative to the sheath to bend the needle about the predetermined bend radius. After completing the bend, the tool is removed from the needle and disposed of.

7 Claims, 14 Drawing Sheets

Related U.S. Application Data

(60) Provisional application No. 62/862,804, filed on Jun. 18, 2019.

(56) References Cited

U.S. PATENT DOCUMENTS

| | | | | |
|---|---|---|---|---|
| 3,168,118 A | * | 2/1965 | Holman | B65B 13/285 |
| | | | | 140/149 |
| 4,257,159 A | * | 3/1981 | Wingert | H01R 43/00 |
| | | | | 7/108 |
| 5,771,945 A | * | 6/1998 | Jenner | H01R 43/28 |
| | | | | 140/123 |
| 2007/0215234 A1 | * | 9/2007 | Poole | H01R 43/28 |
| | | | | 140/118 |

OTHER PUBLICATIONS

Chinese First Office Action—Application No. 201980031880.X & Search Report—dated Sep. 26, 2023.

* cited by examiner

BENDING TOOLS AND METHODS OF USE THEREOF

CROSS-REFERENCE TO RELATED APPLICATIONS

This application is a continuation-in-part of International Application No. PCT/US20/35675, filed Jun. 2, 2020, entitled BENDING TOOLS AND METHODS OF USE THEREOF, which in turn claims priority to and benefit of U.S. Provisional Application No. 62/862,804, filed Jun. 18, 2019, the contents of each of which are incorporated herein by reference in their entirety for all purposes.

FIELD

The present disclosure relates generally to bending tools and, more particularly, to bending tools for bending a surgical needle.

BACKGROUND

Surgical devices have been developed in which a cannulated needle is slidably mounted in a protective sheath attached to a handle. One or more anchors may be disposed within the needle to be expelled from the distal end of the needle for closing a wound or tear in soft tissue. While both straight and curved needles are known in the art, in some cases, there is a user need to bend the needle beyond what is currently available. For example, an increased bend in the distal end of the needle may grant better access to tears in the posterior to middle-third region of the menisci, while a bend in the proximal portion of the needle allows for maneuvering around the intercondylar eminences of the tibial plateau.

Some surgical needles have been provided with flexible distal ends, as well as a means for bending the needles in a predetermined direction. However, such surgical needles have been found to be unduly expensive and complicated. In surgical needles that are not flexible, users may sometimes bend the needle "off-label" by hand or using forceps, which not only puts the user at risk, but risks damaging the needle beyond use. For example, the off-label bending may put a kink in the needle or crush the needle tip, which could prevent deployment of anchors inserted within the needle.

SUMMARY

Described herein is a single-patient-use disposable tool that allows for bending of the needle, while limiting and controlling the maximum bend angle and bend radius of the needle. The tool can be pre-installed on a needle or can be provided as a separate piece. The tool comprises a molded, single-piece body with a curved upper surface having a predetermined bend radius for bending a needle slidably disposed in a sheath. A distal end of the curved surface has a slot for insertion the needle tip, while the proximal end of the curved surface has a guide member for slidably receiving the sheath. Two finger loops or similar ergonomic features allow the user to rotate the bending tool relative to the sheath to bend the needle about the predetermined bend radius. After completing the bend, the tool is removed from the needle and disposed of.

Examples of the bending tool of this disclosure may include one or more of the following, in any suitable combination.

In examples, a bending tool of this disclosure includes a body having a curved surface extending between a proximal and distal end. The tool also includes a slot at the distal end of the curved surface for receiving a tip of a needle. The tool also includes a guide portion for receiving a sheath of the needle therethrough. When the tip of the needle is inserted into the slot, the guide portion allows for bending of the shaft of the needle along the curved surface of the body when the body is rotated toward a shaft of the needle.

In further examples, the body is molded as a single piece. In examples, the body includes an angle limiter adjacent the curved surface for limiting a maximum bend angle or bend radius of the needle. In examples, the curved surface has a predetermined bend radius or bend angle. In examples, the body includes markings for indicating the predetermined bend radius or bend angle of the curved surface. In examples, the body comprises a textured gripping surface. In examples, a width of the curved surface of the body is selected to be substantially equal to a width of the sheath. In examples, the body is made of an injection molded plastic. In examples, the tool is preassembled to the tip of the needle. In examples, the needle is a cannulated needle. In examples, the guide portion further includes a window for direct visualization of the needle. In examples, the guide portion includes a curved surface. When the tip of the needle is inserted into the slot, the guide portion further allows for bending of the shaft of the needle along the curved surface of the guide portion when the body is rotated away from the shaft of the needle.

In examples, methods of bending a needle of this disclosure include inserting a tip of a needle into a slot of a bending tool. The bending tool includes a body having a curved surface extending between a proximal and distal end. The slot is located at the distal end of the curved surface. The tool also includes a guide portion for receiving a sheath of the needle therethrough. The method further includes rotating the body toward a shaft of the needle such that the shaft of the needle is bent along the curved surface of the body. In further examples, the needle is a cannulated needle. In examples, the method further includes limiting a maximum bend angle or bend radius of the needle with an angle limiter adjacent the curved surface. In examples, the method further includes disposing of the tool after bending the shaft of the needle.

In examples, a bending tool of this disclosure includes a body having a proximal end, a distal end, and a longitudinal axis extending therebetween. The body has a slot extending through the body transverse to the longitudinal axis. The slot is configured to receive a shaft of a needle. The slot includes at least one curved surface extending at an angle from the longitudinal axis. When the shaft of the needle is inserted into the slot, the tool allows for bending of the shaft along the curved surface. In examples, the slot is configured to provide three contact points on the shaft of the needle when the needle is inserted into the slot.

In examples, a bending tool of this disclosure includes a body having a proximal end, a distal end and a longitudinal axis extending therebetween. A first slot extends through the body along the longitudinal axis. A proximal end of the first slot has a first curved surface extending at an angle from the longitudinal axis. A distal end of the first slot is configured to receive a tip of a needle. A second slot extends through the body transverse to the longitudinal axis. The second slot includes a second curved surface extending at an angle from the longitudinal axis. The second slot is configured to receive a shaft of the needle. When the tip of the needle is inserted into the distal end of the first slot, the slot allows for bending of the tip of the needle along the first curved surface. When the shaft of the needle is inserted into the second slot, the second slot allows for bending of the shaft along the second curved surface. In examples, the first slot includes a relief channel configured to provide clearance for one or more implants and/or suture disposed within the tip of the needle.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein.

DETAILED DESCRIPTION

Figure 1A:
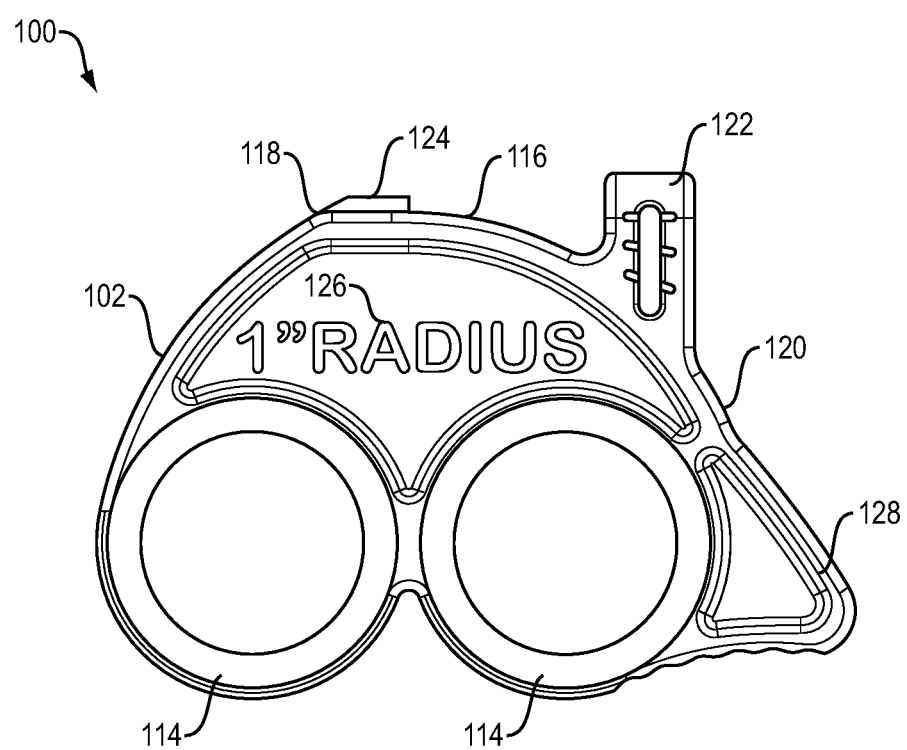
FIG. 1A is a side view of an example of the bending tool of this disclosure.

In the description that follows, like components have been given the same reference numerals, regardless of whether they are shown in different examples. To illustrate example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used to represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts. Use of the terms "upper," "lower," and the like is intended only to help in the clear description of the present disclosure and are not intended to limit the structure, positioning and/or operation of the disclosure in any manner.

Turning now to FIG. 1A, an example of the bending tool 100 of the present disclosure is shown in a side view. The bending tool 100 is comprised of a substantially flat body 102 including an upper curved surface 116 having a width approximately equal to a sheath of a cannulated needle. In examples, the body 102 is made of an injection molded plastic, such as acrylonitrile butadiene styrene (ABS) or polycarbonate. A lower portion of the body 102 includes two finger loops 114 or similar ergonomic features to allow the user to manipulate the bending tool 100. The curved surface 116 extends between a proximal end 120 and a distal end 118 of the curved surface 116. A guide portion 122 at the proximal end 120 of the curved surface 116 is configured for receiving the sheath of the needle therethrough. A retaining slot 124 at the distal end 118 of the curved surface 116 is configured to receiving the tip of the needle. In examples where the bending tool 100 is preassembled to the needle, the slot 124 also serves as a sharps safety protector cap for the needle tip. The retaining slot 124 is spaced from the finger loops 114 to reduce user risk by positioning the hand away from the sharp needle tip. The radius of the curved surface 116 is selected such that it has a maximum predetermined bend radius for controlling the degree of bending of the needle, as further described below. The body 102 may also comprise markers or indicia 126 for indicating the predetermined bend radius (for example, one inch, as shown) of the bending tool 100. An angle limiter 128 is furthermore disposed below the curved surface 116 to limit the maximum bend angle or bend radius of the needle.

Figure 1B:
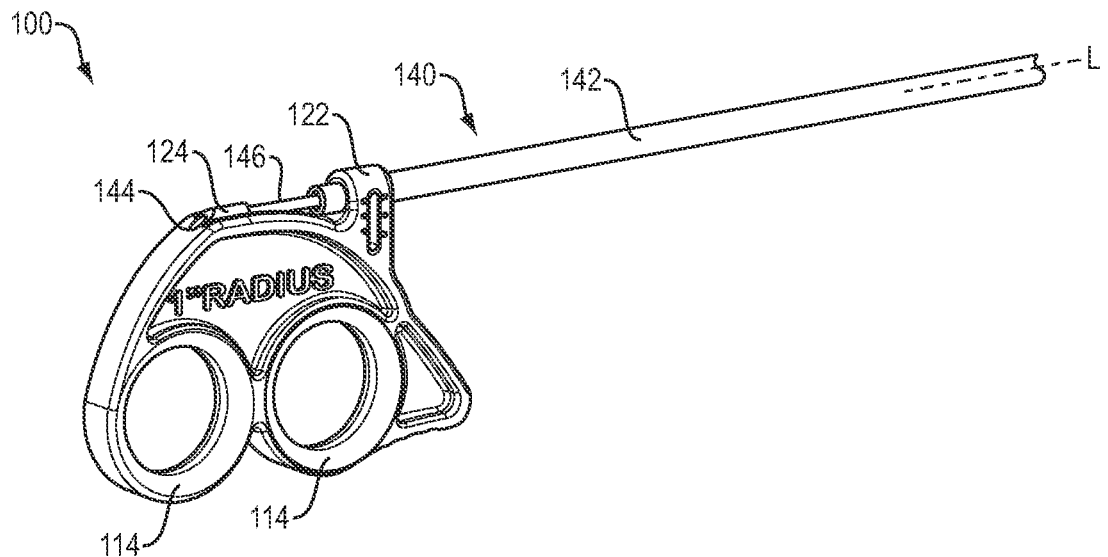
FIGS. 1B-D illustrate the use of the bending tool of FIG. 1A in bending a cannulated needle.
Figure 1C:
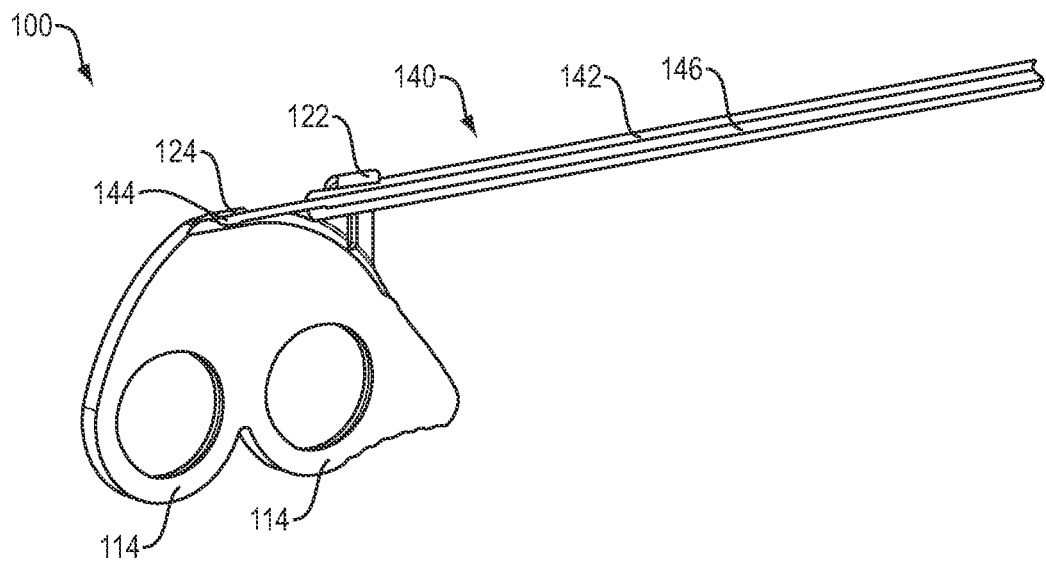

Operation and use of the bending tool 100 will now be described with regard to FIGS. 1B and 1C in the bending of a surgical needle 140, such as the needles described in U.S. Pat. Nos. 7,153,312, 7,887,551, 8,512,375 and 7,651,509 to Smith & Nephew, Inc. (Memphis, TN), the disclosures of which are incorporated herein by reference. FIG. 1B illustrates the use of the bending tool 100 in a perspective view, while FIG. 1C illustrates the use of the bending tool 100 in a cross-sectional view. In examples, the bending tool 100 is pre-attached to the needle 140 such that the sharp, beveled end 144 of the needle 140 is disposed within the slot 124 and the sheath 142 extends through the guide portion 122. Let it be assumed that the user wishes to access a repair site in which the needle 140 is desired to be directed at an angle with respect to the longitudinal axis L of the sheath 142. Thus, it is desired to place a bend in the shaft 146 of the needle 140. This can be accomplished by the user holding the handle (not shown) of the needle 140 in one hand and then grasping the finger loops 114 of the bending tool 100 in the other hand.

Figure 1D:
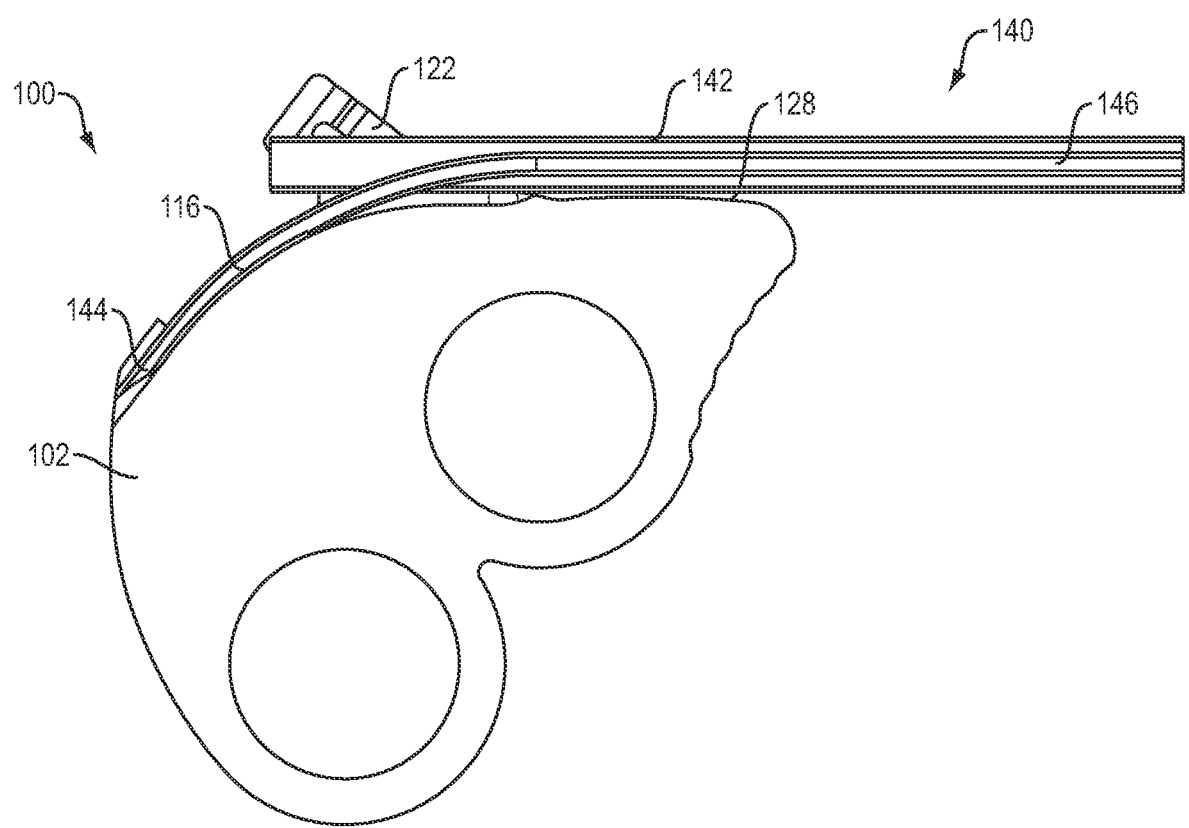

As shown in FIG. 1D, while holding the needle 140 in a stationary position, the bending tool 100 can be rotated in a direction toward the shaft 146 of the needle 140. The guide portion 122 is configured to allow the sheath 142 to move toward the curved surface 116 such that the shaft 146 of the needle 140 bends along the curved surface 116. The user continues to rotate the bending tool 100 until the desired amount of bend has been placed in the shaft 146 of the needle 140. In examples where the sheath 142 is made of a thin plastic, the sheath 142 may flex with the needle 140 as the needle 140 is bent to the desired shape. The angle limiter 128 limits the maximum bend angle or bend radius of the needle 140. The bend of the shaft 146 has a predetermined bend radius as determined by the curved surface 116, thereby ensuring that undue stresses are not placed in the needle 140. By providing a predetermined bend radius for the curved surface 116, it is possible to bend the shaft 146 of the needle 140 within predetermined limits, while at the same time preventing collapsing or kinking of the needle 140 or crushing of the needle tip 144. After the desired amount of bend has been placed in the shaft 146 of the needle 140, the bending tool 100 can be removed from the needle 140 and disposed of. The needle 140 is then ready for use.

Figure 2A:
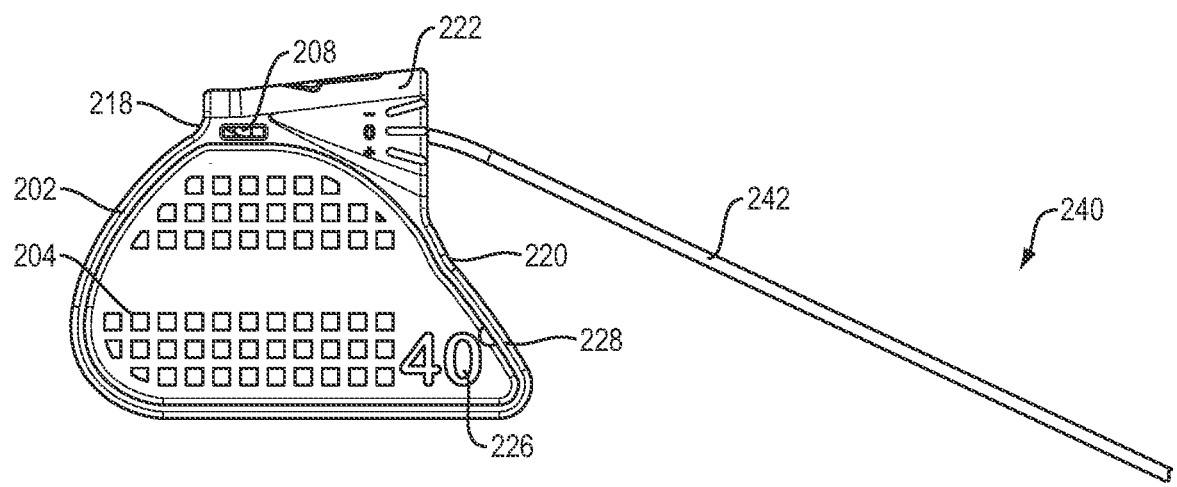
FIGS. 2A and 2B illustrate another example of the bending tool of this disclosure in a side view (FIG. 2A) and perspective view (FIG. 2B)
Figure 2B:
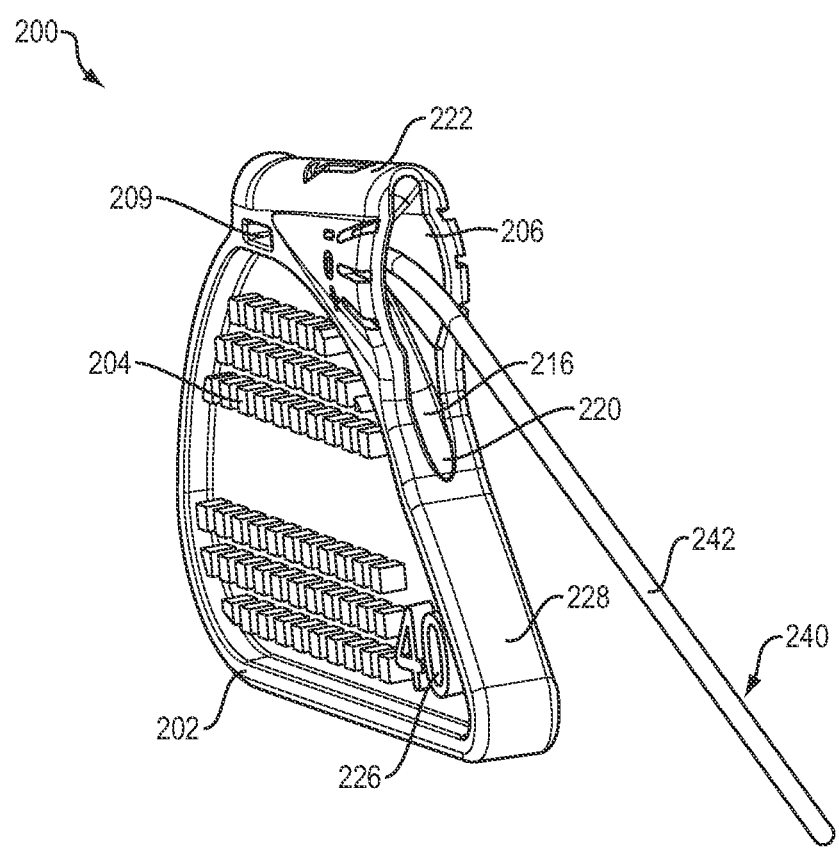

Turning now to FIGS. 2A and 2B, another example of the bending tool 200 of the present disclosure is shown in a side view and a perspective view, respectively. The bending tool 200 is substantially similar to the bending tool 100, except as described below. The bending tool is comprised of a substantially flat body 202 including a first curved surface 216 (FIG. 2B) having a width approximately equal to a sheath 242 of a cannulated needle 240. In examples, the body 202 may include a textured surface 204, such as a waffle pattern (as shown), to aid in gripping the body 202. The body 202 may also comprise markers or indicia 226 for indicating the predetermined bend angle of the needle 240 (as opposed to the predetermined bend radius of the bending tool 100). The first curved surface 216 extends between a proximal end 220 and a distal end 218 of the first curved surface 216 and includes a relief in curvature for implant/suture clearance. An angle limiter 228 is furthermore disposed below the first curved surface 216 to limit the maximum bend angle or bend radius of the needle 240. A guide portion 222 is configured for receiving the sheath 242 of the needle 240 therethrough. The guide portion 222 includes a window 209 for direct visualization of the needle 240 through the guide portion 222.

Figure 2C:
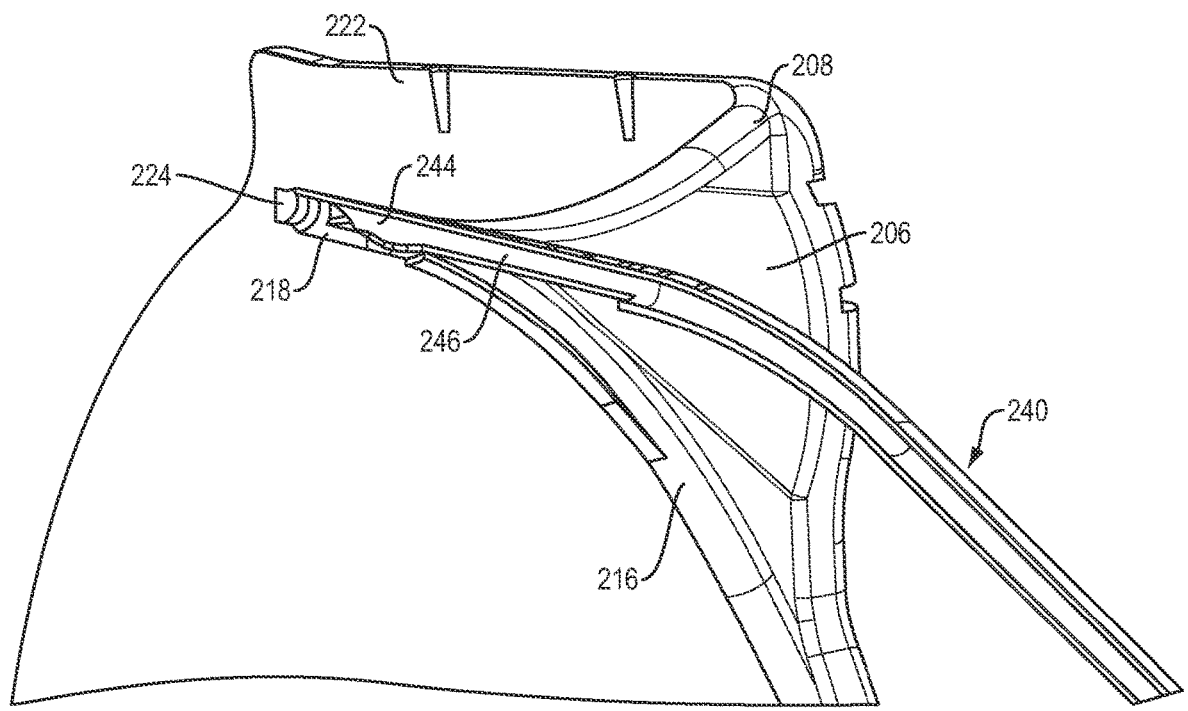
FIG. 2C is a cross-sectional view of the bending tool of FIGS. 2A and 2B.

As shown in FIG. 2C, the guide portion 222 also includes a second curved surface 208 extending away from the first curved surface 216 of the body 202. A retaining slot 224 within the guide portion 222 at the distal end 218 of the first curved surface 216 is configured to receiving the tip 244 of the needle 240. When the tip 244 is inserted into the slot 224, an opening 206 at the proximal end of the guide portion 222 is configured to allow the shaft 246 of the needle 240 to be bent along the first curved surface 216 by rotating the body 202 toward the shaft 246 of the needle 240, or along the second curved surface 208 by rotating the body 202 away from the shaft 246 of the needle 240, as desired.

Figure 3A:
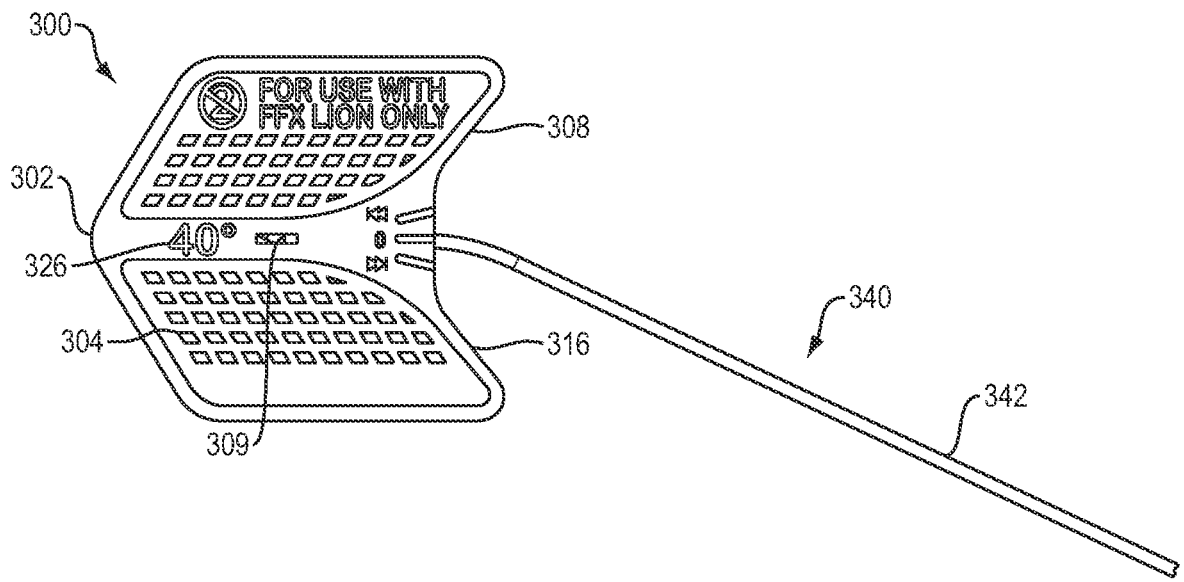
FIGS. 3A and 3B illustrate another example of the bending tool of this disclosure in a side view (FIG. 3A) and a cross-sectional view (FIG. 3B)
Figure 3B:
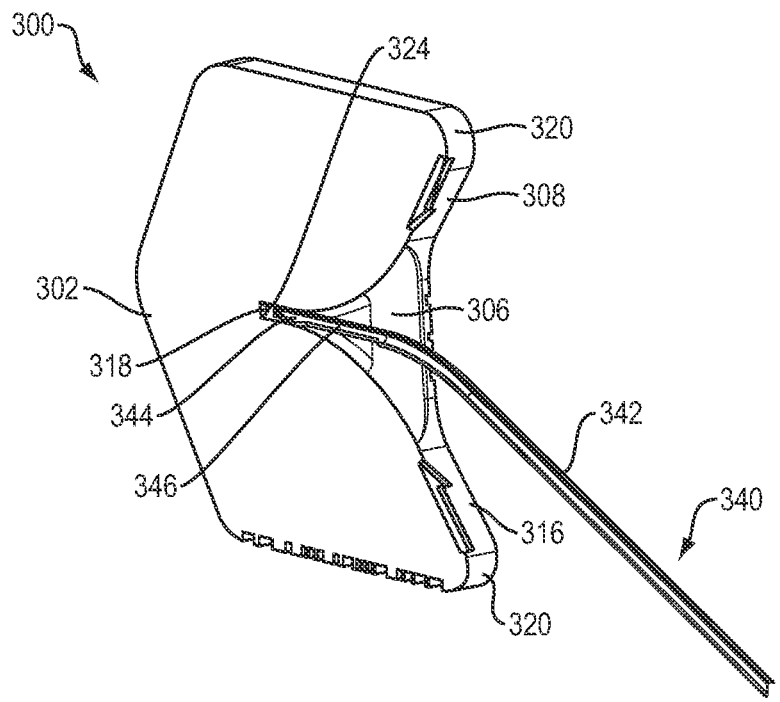

Turning now to FIGS. 3A and 3B, another example of the bending tool 300 of the present disclosure is shown in a side view and a cross-sectional view, respectively. The bending tool 300 is substantially similar to the bending tool 200, except as described below. The bending tool 300 is comprised of a substantially flat body 302 including a first curved surface 316 and a second curved surface 308. In examples, the body 302 may include a textured surface 304, such as a waffle pattern (as shown), to aid in gripping the body 302. The body 302 may also comprise markers or indicia 326 for indicating the predetermined bend angle of the needle 340. An opening 306 at the proximal end 320 of the body 302 is configured for receiving the sheath 342 of the needle 340 therethrough. A retaining slot 324 within the body 302 at the distal end 318 of the curved surfaces 308, 316 is configured to receiving the tip 344 of the needle 340.

The body 302 may define a window 309 for direct visualization of the needle 340 in the retaining slot 324. When the tip 344 is inserted into the slot 324, the opening 306 allows the shaft 346 of the needle 340 to be bent along the first curved surface 316 by rotating the body 302 toward the shaft 346 of the needle 340, or along the second curved surface 308 by rotating the body 302 away from the shaft 346 of the needle 340, as desired.

Figure 4A:
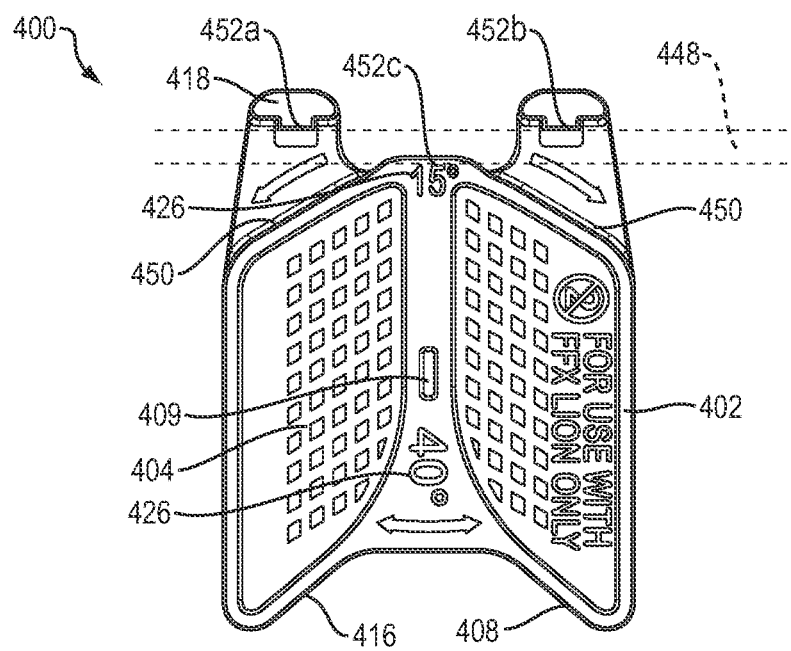
FIGS. 4A and 4B illustrate another example of the bending tool of this disclosure in opposing side views.
Figure 4B:
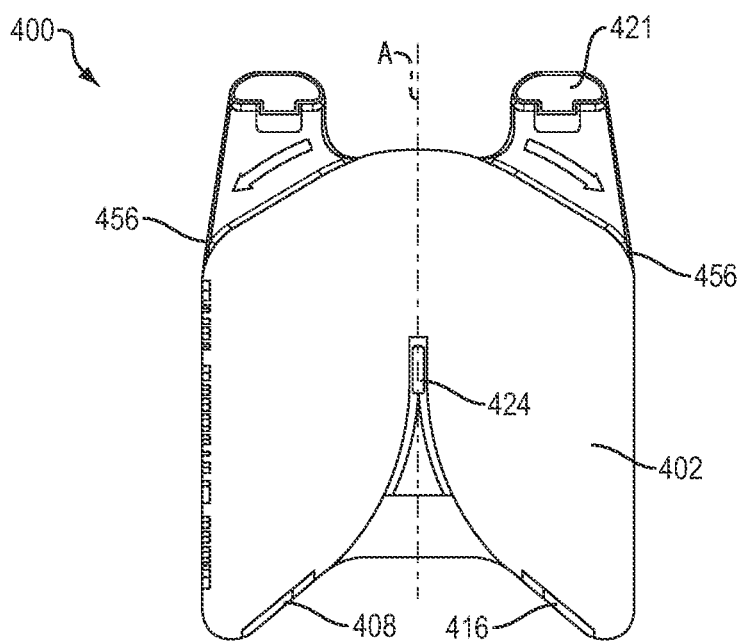

Turning now to FIGS. 4A and 4B, another example of the bending tool 400 of the present disclosure is shown in opposing side views. The bending tool 400 is substantially similar to the bending tool 300, except as described below. However, the bending tool 400 is advantageously configured to allow proximal bending of a shaft of a needle, as well as distal bending of the tip of the needle. As shown in FIGS. 4A and 4B, the bending tool 400 is comprised of a substantially flat body 402 including a first curved surface 416 and a second curved surface 408. In examples, the body 402 may include a textured surface 404 to aid in gripping the body 402. The body 402 may also comprise markers or indicia 426 for indicating the predetermined bend angle of the needle (not shown). A first retaining slot 424 within the body 402 extends along a longitudinal axis A of the body 402 and is configured for bending the tip of the needle. In examples, the body 402 may define a window 409 for direct visualization of the needle in the first retaining slot 424. The body 402 further comprises a second retaining slot 448 extending through the body 402 transverse to the longitudinal axis A configured to receive the shaft of the needle. In examples, the second retaining slot 448 extends through the distal end 421 of the body 402, as shown.

Still referring to FIGS. 4A and 4B, the second retaining slot 448 includes at least a third curved surface 450 extending at an angle from the longitudinal axis A. An angle limiter 456 is furthermore disposed at an outside end of the third curved surface 450 to limit the maximum bend angle or bend radius of the needle. When the shaft of the needle is inserted into the second retaining slot 448, the tool 400 allows for bending of the shaft along the curved surface 450 by rotating the body 402 toward the needle in either direction. Notably, in examples, the body 402 is configured to provide three contact points 452a,b,c on the needle. The contact points 452a,b are provided on the distal side of the second retaining slot 448, while the contact point 452c is provided on the proximal side of the second retaining slot 448. However, more or fewer than three contact points are contemplated by this disclosure. Once the bend is initiated, the user's hand becomes the contact point 452a or 452b, depending on the direction of the bend. After completing the bend to the user's liking, the tool 400 is then removed and disposed of.

Figure 5A:
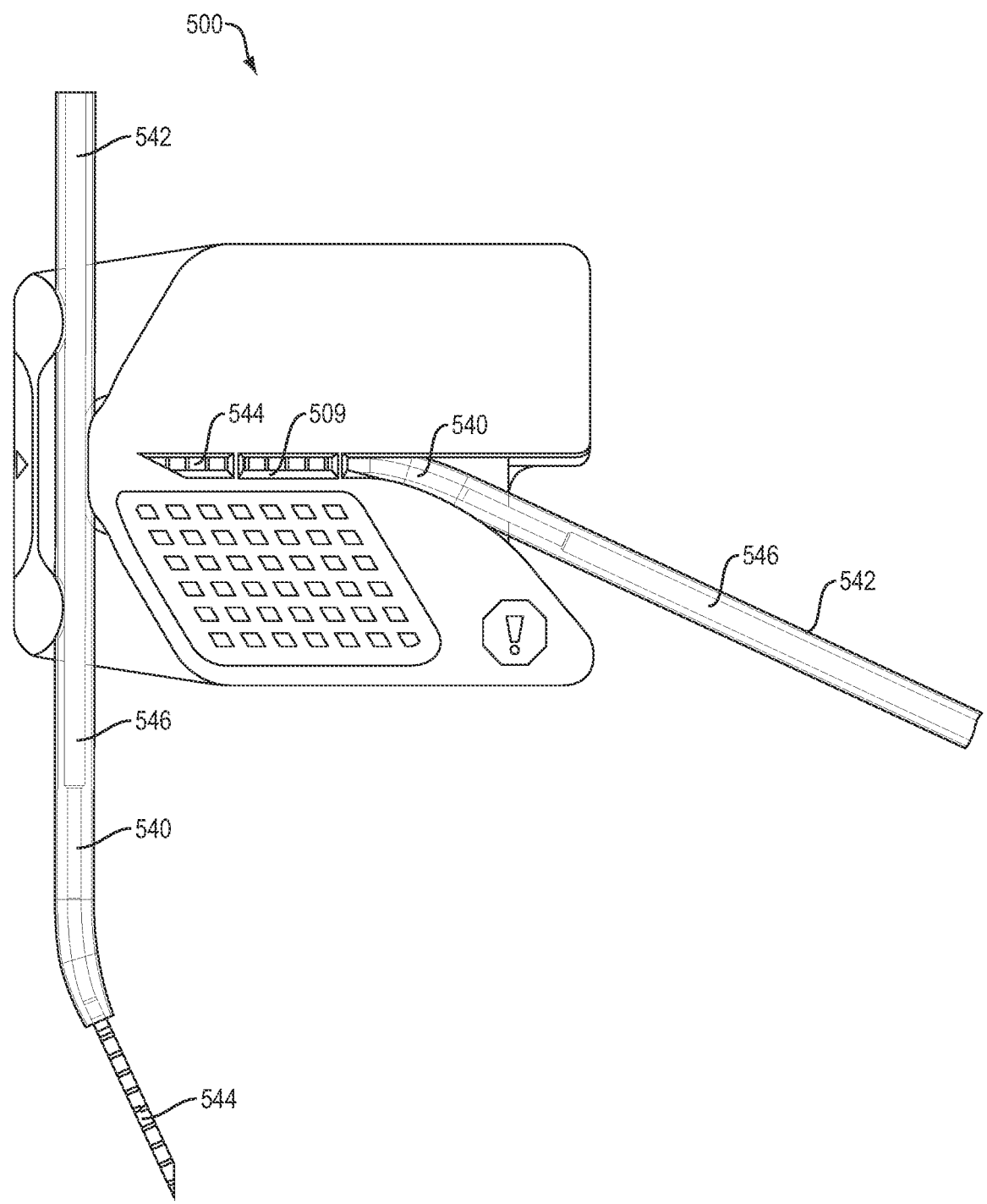
FIGS. 5A-D illustrate another example of the bending tool of this disclosure in various views.
Figure 5B:
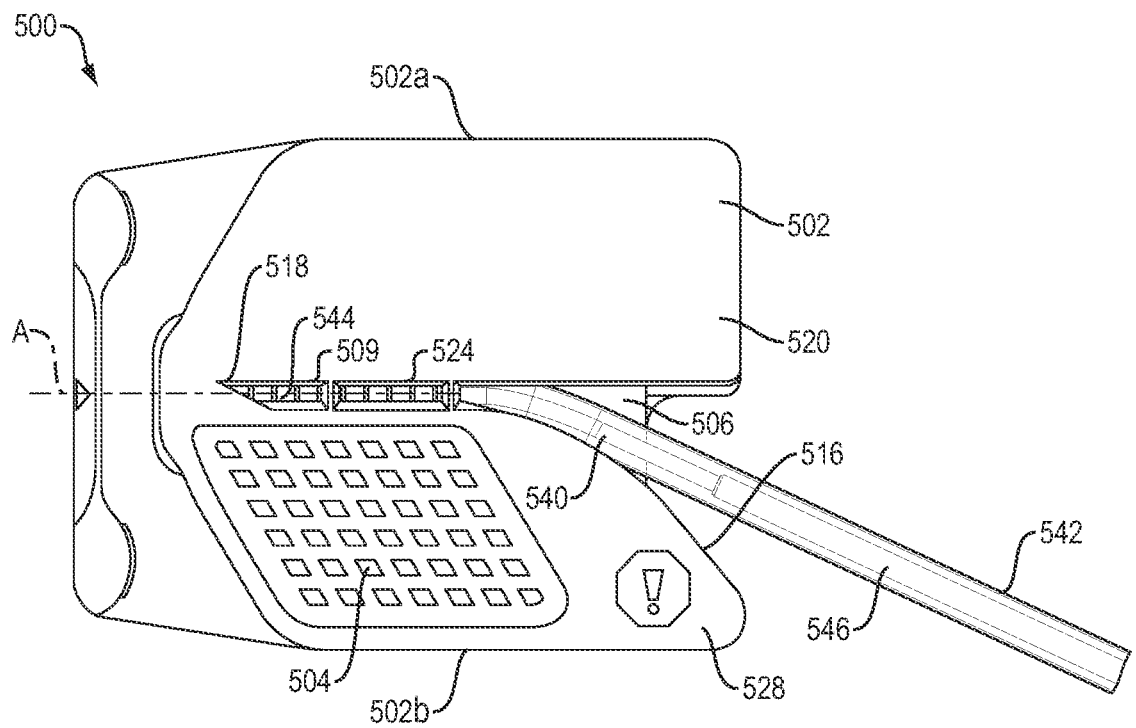

Turning now to FIG. 5A, another example of the bending tool 500 of the present disclosure is shown in a side view. The bending tool 500 is substantially similar to the bending tool 400, except as described below. The bending tool 500 is configured to allow proximal bending of a shaft 546 of a needle 540, as well as distal bending of the tip 544 of the needle 540. As shown in FIG. 5B, the bending tool 500 is comprised of a substantially flat body 502 including a first curved surface 516. In examples, the body 502 may include a textured surface 504, such as a waffle pattern, to aid in gripping the body 502. An opening 506 at the proximal end 520 of the body 502 is configured for receiving the sheath 542 of the needle 540. A first retaining slot 524 extends along the longitudinal axis A of the body 502 at the distal end 518 of the first curved surface 516. The first retaining slot 524 is located substantially equidistant between a first side 502a and a second side 502b of the body 502 and is configured to receiving the tip 544 of the needle 540. In examples, the body 502 may define a window 509 for direct visualization of the needle in the first retaining slot 524. When the tip 544 is inserted into the slot 524, the opening 506 allows the shaft 546 of the needle 540 to be bent along the first curved surface 516 by rotating the body 502 toward the shaft 546 of the needle 540. An angle limiter 528 is furthermore disposed below the first curved surface 516 to limit the maximum bend angle or bend radius of the needle 540.

Figure 5C:
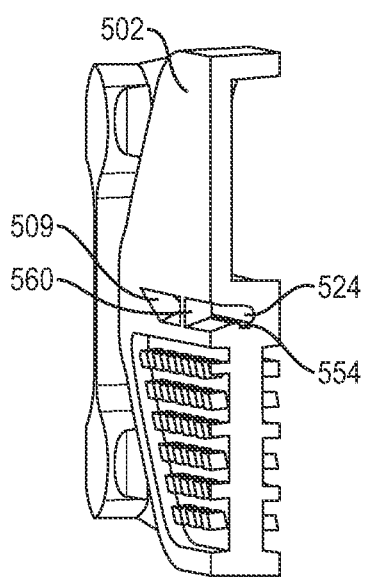

As shown in FIG. 5C, the first retaining slot 524 may also include a relief channel 554 which provides clearance for any implants disposed within tip 544 of the needle (not shown) and/or any sutures attached thereto, such that the implants and/or suture will not be subjected to the stresses incurred during bending of the tip of the needle. The window 509 may also comprise one or more bridge features 560 to prevent the needle from inadvertently sliding out of the first retaining slot 524 during bending of the needle and potentially creating a needle stick hazard. The bridge features 560 also provide structural support for the window 509.

Figure 5D:
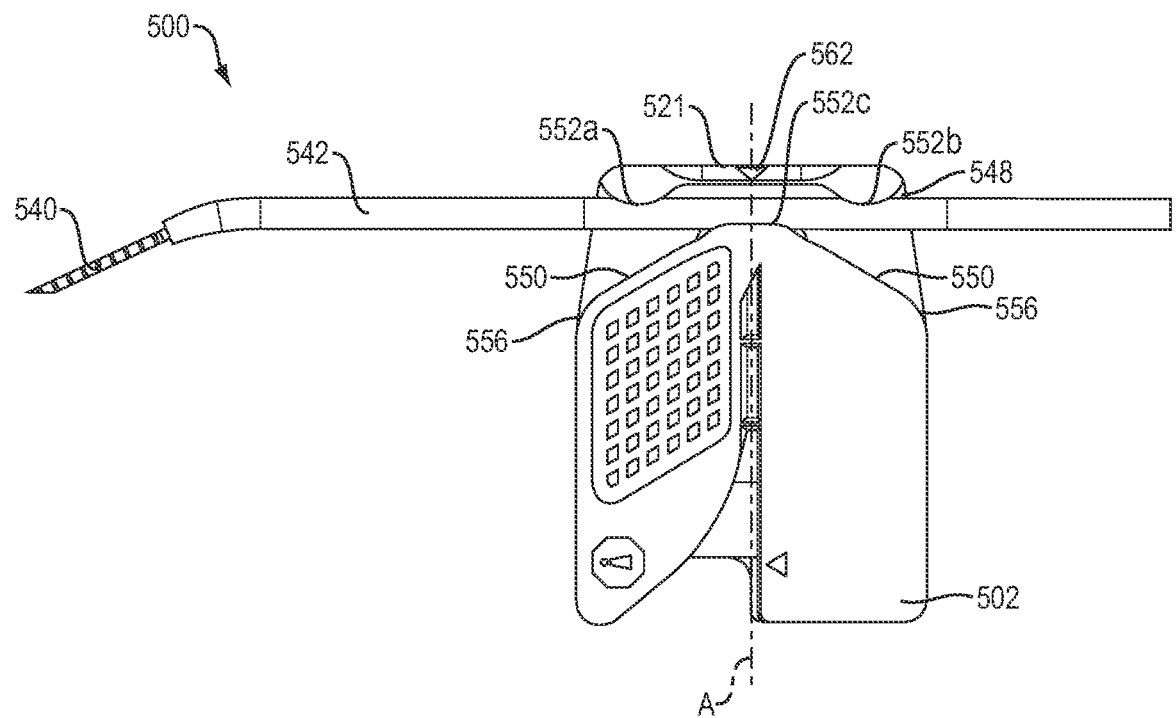

Turning now to FIG. 5D, the body 502 further comprises a second retaining slot 548 extending through the body 502 transverse to the longitudinal axis A. The second retaining slot 548 is configured to receive the sheath 542 of the needle 540. In examples, the second retaining slot 548 extends through the distal end 521 of the body 502, as shown. The second retaining slot 548 includes at least a second curved surface 550 extending at an angle from the longitudinal axis A. An angle limiter 556 is furthermore disposed at an outside end of the second curved surface 550 to limit the maximum bend angle or bend radius of the needle 540. When the sheath 542 of the needle 540 is inserted into the second retaining slot 548, the tool 500 allows for bending of the shaft of the needle 540 along the second curved surface 550 by rotating the body 502 toward the needle 540 in either direction. Notably, in examples, the body 502 is configured to provide three contact points 552*a,b,c* on the needle 540. The contact points 552*a,b* are provided on the distal side of the second retaining slot 548, while the contact point 552*c* is provided on the proximal side of the second retaining slot 548. However, more or fewer than three contact points are contemplated by this disclosure. Once the bend is initiated, the user's hand becomes the contact point 552*a* or 552*b*, depending on the direction of the bend. In examples, the distal end 521 of the body 502 also includes a printed arrow 562 where the three contact points 552*a,b,c* line up with a corresponding mark on the needle 542 to indicate a "no-bend" zone, thus minimizing bending at the weakest point in the needle 540. After completing the bend to the user's liking, the tool 500 is then removed and disposed of.

Figure 5E:
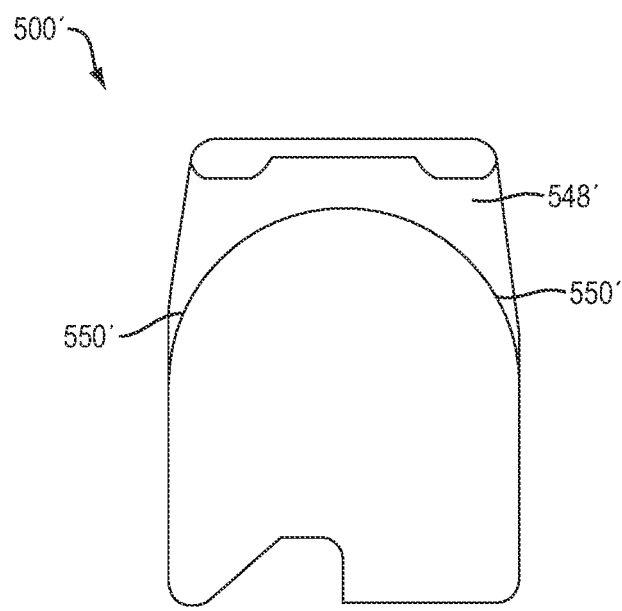
FIG. 5E illustrates an alternative example of the bending tool of FIGS. 5A-D.

An alternative example of the bending tool 500' is shown in FIG. 5E. Like the body 502 of bending tool 500, the body 502' includes a second retaining slot 548' extending through the body 502' and a second curved surface 550'. However, in the bending tool 500', the second curved surface 550' does not include an angle limiter at the end of the second curved surface 550'. Thus, the bending tool 500' controls the bend radius but does not limit the bend angle of the needle when the needle is bent along the second curved surface 550'. It is also contemplated by this disclosure that the bending tool may control the bend angle but not the bend radius of the needle.

Figure 6A:
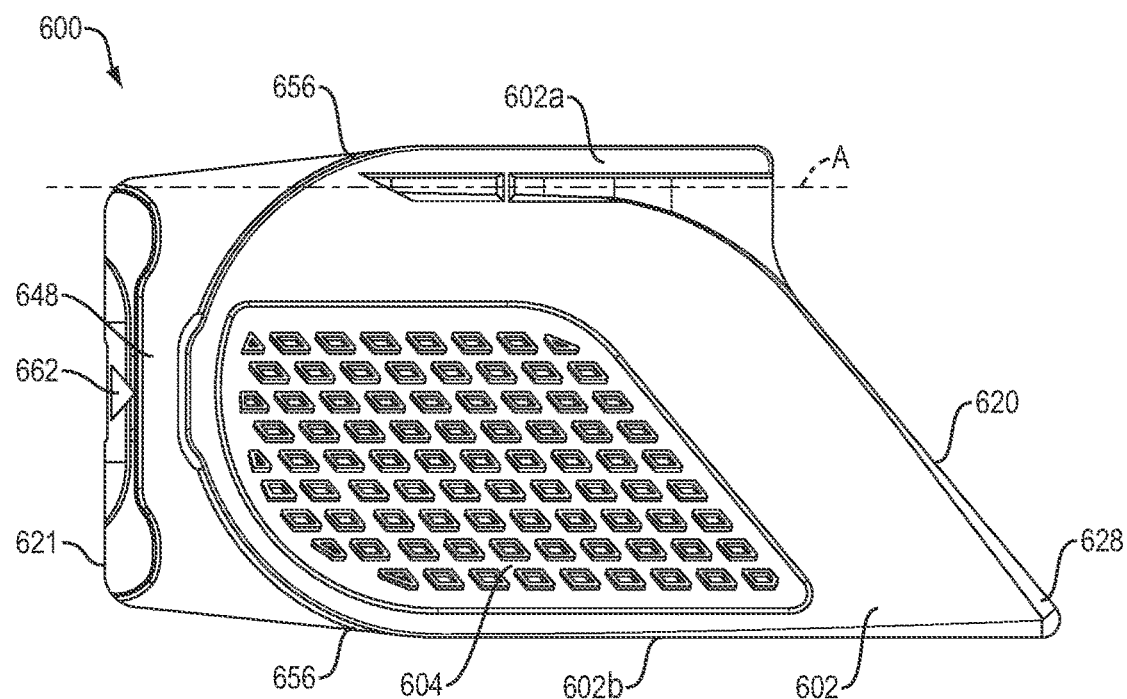
FIGS. 6A and 6B illustrate another example of the bending tool of this disclosure in a side view (FIG. 6A) and a perspective view (FIG. 6B)
Figure 6B:
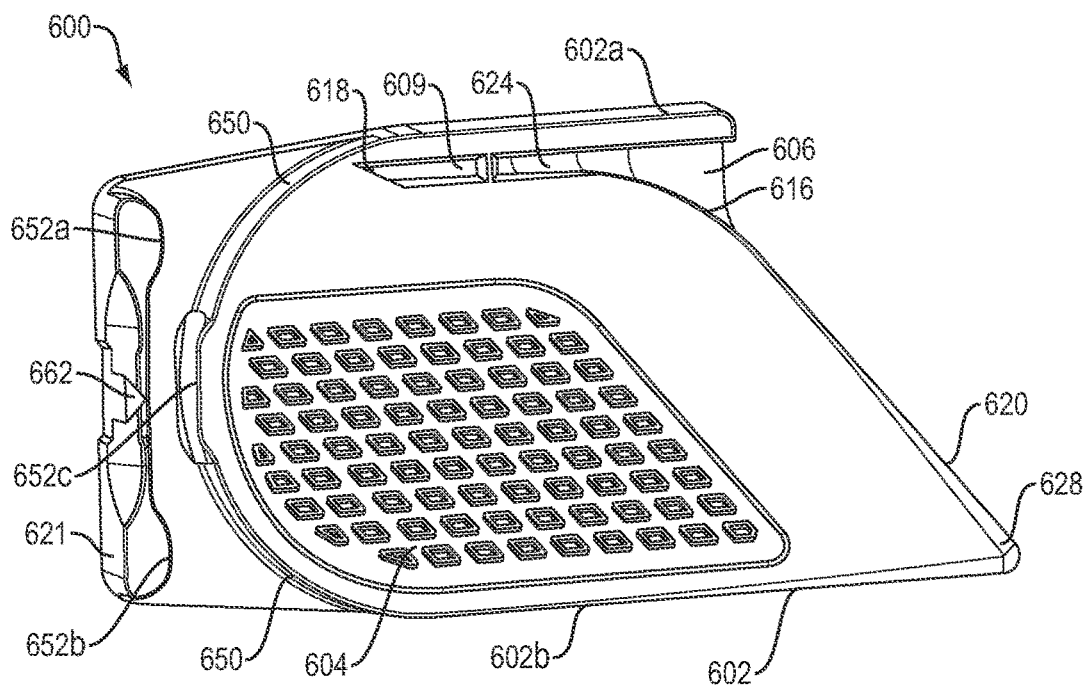

Turning now to FIGS. 6A and 6B, another example of the bending tool 600 of the present disclosure is shown in a side view (FIG. 6A) and a perspective view (FIG. 6B). The bending tool 600 is substantially similar to the bending tool 500, except as described below. The bending tool 600 is configured to allow proximal bending of a shaft of a needle (not shown), as well as distal bending of the tip of the needle. The bending tool 600 is comprised of a substantially flat body 602 including a first curved surface 616. In examples, the body 602 may include a textured surface 604, such as a waffle pattern, to aid in gripping the body 602. An opening 606 at the proximal end 620 of the body 602 is configured for receiving a sheath of the needle. A first retaining slot 624 extends along the longitudinal axis A of the body 602 at the distal end 618 of the first curved surface 616. The first retaining slot 624 is located closer to a first side 602*a* than to a second side 602*b* of the body 602 and is configured to receiving the tip of the needle. In examples, the body 602 may define a window 609 for direct visualization of the needle in the first retaining slot 624. When the tip of the needle is inserted into the slot 624, the opening 606 allows the shaft of the needle to be bent along the first curved surface 616 by rotating the body 602 toward the shaft of the needle. An angle limiter 628 is furthermore disposed below the first curved surface 616 to limit the maximum bend angle or bend radius of the needle.

Still referring to FIGS. 6A and 6B, the body 602 further comprises a second retaining slot 648 extending through the body 602 transverse to the longitudinal axis A. The second retaining slot 648 is configured to receive the sheath of the needle. In examples, the second retaining slot 648 extends through the distal end 621 of the body 602, as shown. The second retaining slot 648 includes at least a second curved surface 650 extending at an angle from the longitudinal axis A. An angle limiter 656 is furthermore disposed at an outside end of the second curved surface 650 to limit the maximum bend angle or bend radius of the needle. When the sheath of the needle is inserted into the second retaining slot 648, the tool 600 allows for bending of the shaft of the needle along the second curved surface 650 by rotating the body 602 toward the needle 640 in either direction. In examples, the body 602 is configured to provide three contact points 652*a,b,c* on the needle. The contact points 652*a,b* are provided on the distal side of the second retaining slot 648, while the contact point 652*c* is provided on the proximal side of the second retaining slot 648. However, more or fewer than three contact points are contemplated by this disclosure. Once the bend is initiated, the user's hand becomes the contact point 652*a* or 652*b*, depending on the direction of the bend. In examples, the distal end 621 of the body 602 also includes a printed arrow 662 where the three contact points 652*a,b,c* line up with a corresponding mark on the needle (not shown) to indicate a "no-bend" zone, thus minimizing bending at the weakest point in the needle. After completing the bend to the user's liking, the tool 600 is then removed and disposed of.

Figure 7:
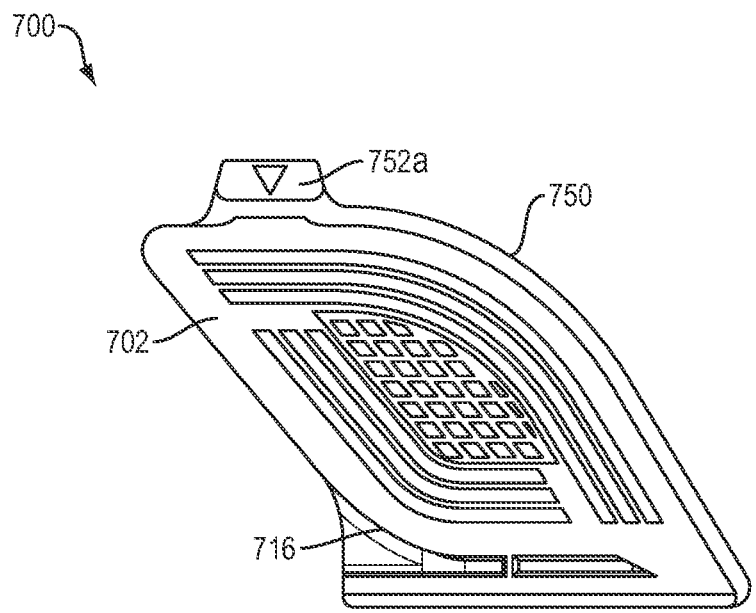
FIG. 7 illustrates an alternative example of the bending tool of this disclosure in a side view.

Turning now to FIG. 7, another example of the bending tool 700 of this disclosure is shown. In the bending tool 700, the body 702 includes a first curved surface 716 at one end of the body 702 for distal bending of a tip of a needle (not shown) and a second curved surface 750 at an opposite end of the body 702 for proximal bending of a shaft of the needle. When the shaft is bent along the curved surface 740, the tool 700 may provide only one contact point 752*a* on the needle.

Figure 8:
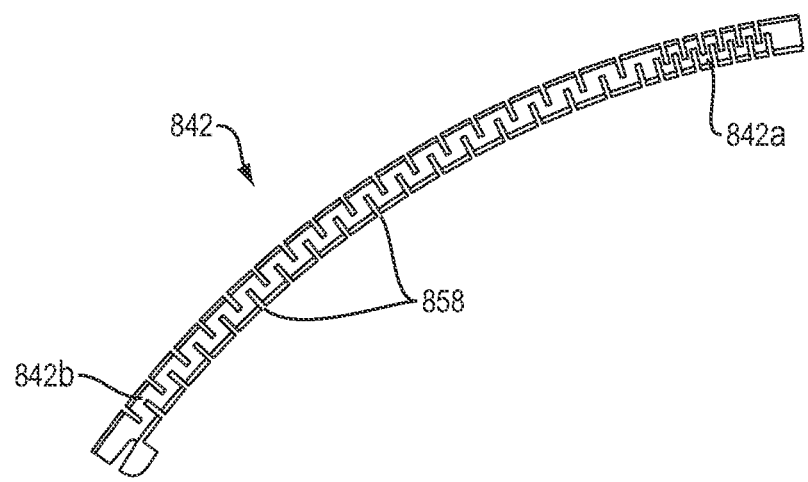
FIG. 8 illustrates an example of a sheath for use with the bending tool of this disclosure.

Turning now to FIG. 8 an example of a sheath 842 of this disclosure is shown. The sheath 842 is configured to slide over the needle (not shown) and control the bend angle and bend radius of the needle via a plurality of slots or notches 858 cut into the wall of the sheath 842. Closer-set notches 858 (shown at end 842*a*) permit a tighter bend angle and bend radius of the needle, while wider-set notches 858 (shown at end 842b) allow for a more gradual bend angle and bend radius of the needle.

Figure 9A:
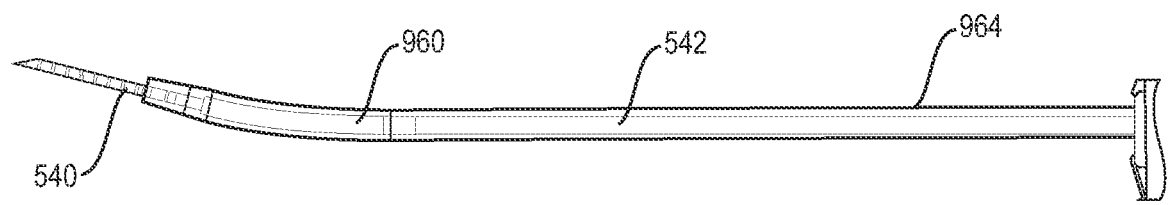
FIGS. 9A-C illustrate an example of a retaining tube and depth tube for use with the bending tool of this disclosure.
Figure 9B:
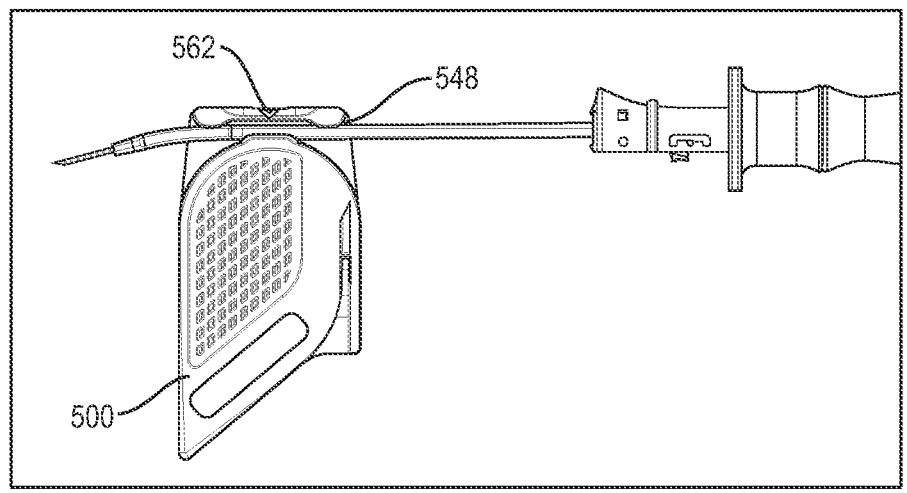

FIG. 9A shows an example of a retaining tube 960 extending through a depth tube 964 of this disclosure. Each of the retaining tube 960 and the depth tube 964 are configured to slide over the needle (for example, needle 540). In examples, the retaining tube 960 is a compliant, extruded tube configured to assemble onto the needle 540 distal to the sheath 542 with a press fit. The retaining tube 960 has a darker color (for example, black) than a color of the depth tube 964. The darker color is selected to be visible through the translucent depth tube 964, which is used to control the insertion depth of the needle 540. A length of the needle 540 covered by the retaining tube 960 represents a "no-bend" zone to the user when the user inserts the needle 540 into the second retaining slot 548 of the bending tool (for example, bending tool 500) (FIG. 9B). The color of the depth tube (for example, orange or pink) is selected to match a color of the appropriate bending tool 500 based on the factory curvature of the needle 540 (e.g., orange for curved and pink for reverse curved). The retaining tube 960 coincides with the printed arrow 562 on the retaining slot 548 when the user positions the needle 540 correctly within the retaining slot 548 for bending, as in FIG. 9B. In contrast, the retaining tube 960 is offset from the printed arrow 562 on the retaining slot 548 when the user positions the needle 540 incorrectly within the retaining slot 548 for bending, as in FIG. 9C. This visual indication advantageously promotes the safe and effective use of the bending tool 500 to modify the needle 540 and preserve the features critical to anchor deployment. The retaining tube 960 also helps manage suture tied to the anchors within the needle 540 to minimize any obstruction of arthroscopic view that can occur between deployment of the anchors or as a result of adjusting the position of the depth tube 964.

Figure 9C:
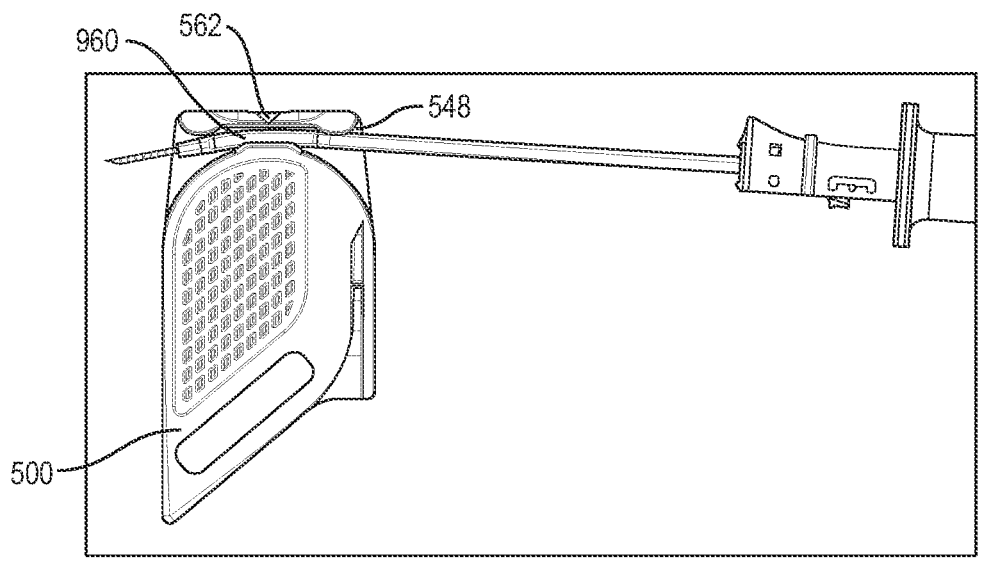

In examples, not shown, the retaining tube 960 could visually indicate the acceptable region for use of the bending tool 500 as opposed to an unacceptable region as shown in FIGS. 9A-C. In examples, the depth tube 964 may consists of visual markings to indicate the acceptable/unacceptable regions for use of the bending tool 500. In examples, the depth tube 964 might be only translucent in a specific region to allow visualization of the retaining tube 960. In examples, the depth tube 964 could include a cutout to allow visualization of the retaining tube 960. In examples, the depth tube 964 could use a temperature or light sensitive colorant to visually indicate an acceptable/unacceptable bending region when the needle 540 is outside the joint space.

Figure 10:
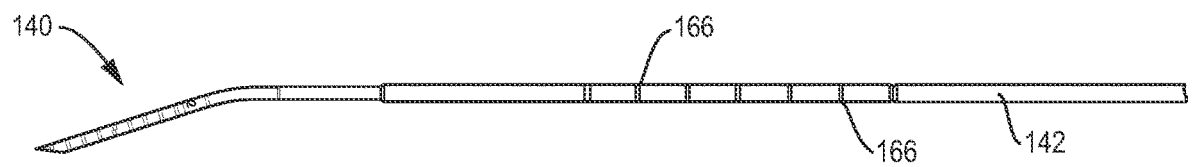
FIG. 10 illustrates another example of a needle for use with the bending tool of this disclosure.

FIG. 10 shows another example of the needle of this disclosure, such as the needle 140. In the example of FIG. 10, the sheath 142 of the needle 140 consists of visual markings 166 that indicate an acceptable region (as shown) for modification with the bending tool. In examples, not shown, the visual markings 166 could also indicate an unacceptable region for modification.

In other examples, not shown, the bending tool of this disclosure could be designed to allow for multiple bend radii. It is further contemplated by this disclosure that the bending tool could be a multi-piece design, and may be used to bend other instruments, including non-cannulated needles. In examples, the bending tool may have a single feature that can be used for both proximal bending of the needle shaft and distal bending of the needle tip. In other examples, the bending tool may comprise moving parts to create the bends in the needle. In further examples, the bending tool may be re-usable. In examples, a design feature may physically preclude the use of the bending tool on certain regions of the needle that impact anchor deployment. In examples, the bending tool may contain symbols or text to convey acceptable/unacceptable regions for needle modification.

One skilled in the art will realize the disclosure may be embodied in other specific forms without departing from the spirit or essential characteristics thereof. The foregoing examples are therefore to be considered in all respects illustrative rather than limiting of the disclosure described herein. Scope of the disclosure is thus indicated by the appended claims, rather than by the foregoing description, and all changes that come within the meaning and range of equivalency of the claims are therefore intended to be embraced therein.

The invention claimed is:

1. A bending tool for a needle having a shaft and a tip, the bending tool comprising:
   a substantially flat body having a proximal end, a distal end and a longitudinal axis extending therebetween;
   a first slot extending along a length of the body, a proximal end of the first slot having a first curved surface extending at an angle from the longitudinal axis, a distal end of the first slot configured to receive a tip of a needle to bend the tip of the needle along the first curved surface;
   a second slot separate and apart from the first slot, the second slot extending across a width of the body, the second slot including a second curved surface extending at an angle from the longitudinal axis, the second slot configured to receive a shaft of the needle to bend the shaft along the second curved surface.

2. The bending tool of claim 1, wherein the first slot includes a relief channel configured to provide clearance for one or more implants and/or suture disposed within the tip of the needle.

3. The bending tool of claim 1, further comprising an angle limiter adjacent the first curved surface for limiting a maximum bend angle or bend radius of the needle.

4. The bending tool of claim 1, wherein the first curved surface has a predetermined bend radius or bend angle.

5. The bending tool of claim 1, wherein the body further comprises a textured gripping surface.

6. The bending tool of claim 1, wherein the first slot includes a window for direct visualization of the needle.

7. The bending tool of claim 1, wherein the second slot is configured to provide three contact points on the needle.

\* \* \* \* \*